United States Patent [19]

Burd et al.

[11] Patent Number: 5,082,768
[45] Date of Patent: Jan. 21, 1992

[54] ATTENUATOR TO SUPPRESS EXTRANEOUS LIGHT IN LUMINESCENT SPECIFIC-BINDING ASSAYS

[75] Inventors: John F. Burd, Mountain View; John W. Dyminski, San Jose; Vincent A. Marinkovich, Palo Alto, all of Calif.

[73] Assignee: Mast Immunosystems, Inc., Mountain View, Calif.

[21] Appl. No.: 639,302

[22] Filed: Dec. 28, 1990

Related U.S. Application Data

[63] Continuation of Ser. No. 621,200, Jun. 15, 1984, abandoned.

[51] Int. Cl.$^5$ .......................................... G01N 33/535
[52] U.S. Cl. .................... 435/7.92; 435/7.93; 435/7.94; 435/975; 436/513; 436/531; 436/825; 436/826; 436/800; 436/808
[58] Field of Search ............... 436/513, 518, 528, 531, 436/825, 826, 800, 806; 435/7.9, 7.92–7.95, 975; 422/61

[56] References Cited

U.S. PATENT DOCUMENTS

| | | | |
|---|---|---|---|
| 4,252,783 | 2/1981 | Kam et al. | 436/825 |
| 4,271,139 | 6/1981 | Hart | 436/531 |
| 4,372,745 | 2/1983 | Mandle et al. | 436/826 |
| 4,380,580 | 4/1983 | Boguslaski et al. | 436/518 |
| 4,390,343 | 6/1983 | Walter | 436/518 |
| 4,421,860 | 12/1983 | Elings et al. | 436/518 |
| 4,435,509 | 3/1984 | Berthold et al. | 436/518 |
| 4,491,634 | 1/1985 | Frezel | 436/518 |
| 4,532,203 | 7/1985 | Ullman et al. | 436/501 |
| 4,582,791 | 4/1986 | Khanna et al. | 436/825 |

OTHER PUBLICATIONS

Nargessi et al., J. Immunol. Meth., 26(1979) 307-313.

Primary Examiner—Christine Nucker
Attorney, Agent, or Firm—Townsend and Townsend

[57] ABSTRACT

An attenuator is included in a reagent medium of a luminescent specific-binding assay to suppress undesirable extraneous light. In one such assay, an analyte in a sample is reacted with a specific binding partner attached to a solid surface, forming an immobilized pair at the surface. One member of the immobilized pair is then allowed to react with a specific binding partner previously conjugated with one component of a luminescent reaction system, and the remaining components are provided in the reagent medium. The resulting light emitted in the luminescent reaction is recorded on photographic film or other photodetector as a measure of the presence and quantity of the analyte in the sample. The reagent medium containing the remaining luminescent reaction system components also includes an attenuator, preferably a dye, which absorbs light over a range of wavelengths including that of the light emitted in the luminescent reaction, the attenuator being present in an amount sufficient to suppress the extraneous light observed adjacent the solid surface in the absence of the attenuator. Reduction of such extraneous light sharpens the recorded luminescent image, thereby allowing a more precise analysis of the light intensity, and additionally reduces the occurrence of false positive images in the assay. In another embodiment, the attenuator preferentially absorbs light emitted in remote portions of a reaction volume so that only light emitted from proximal portions reaches a measurement means. Reactions otherwise requiring a separation step may thereby be conducted homogeneously.

22 Claims, 1 Drawing Sheet

U.S. Patent    Jan. 21, 1992    5,082,768
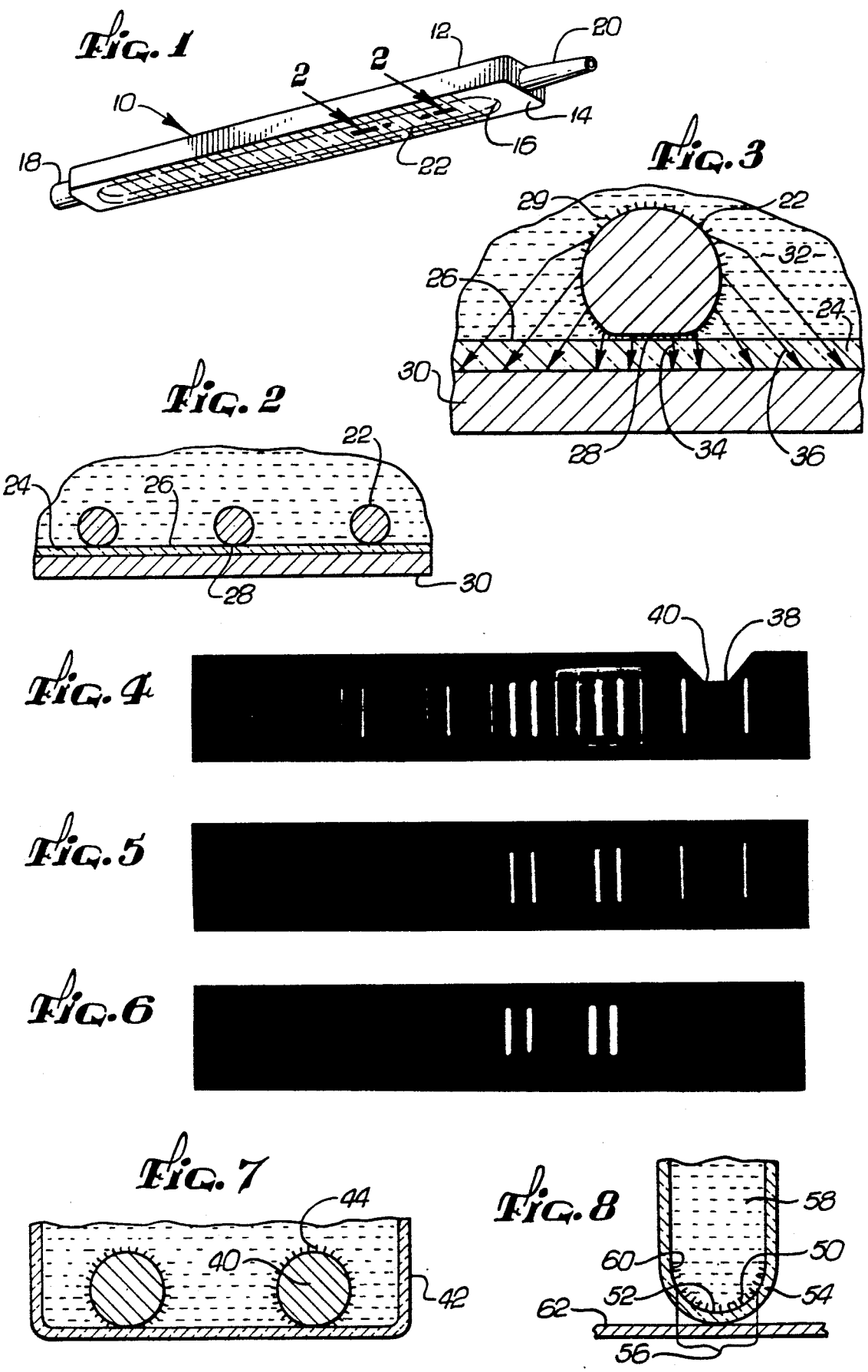

ATTENUATOR TO SUPPRESS EXTRANEOUS LIGHT IN LUMINESCENT SPECIFIC-BINDING ASSAYS

This is a continuation of application Ser. No. 06/621,200, filed June 15, 1984, now abandoned.

BACKGROUND OF THE INVENTION

This invention relates generally to luminescent assay procedures, and, more particularly, to the suppression of extraneous light in luminescent specific binding assays.

Specific binding assays provide an economical means for detecting and measuring an analyte or ligand present in small concentrations in a sample. Specific binding assays are based upon the interaction of two bindable substances, one the analyte and the other a specific binding partner, which specifically recognize each other. Examples of specific binding partners whose interaction can serve as the basis for a specific binding assay include antigens-antibodies, biotinavidin, DNA probes, enzymes-substrates, enzymes-inhibitors, enzymes-cofactors, chelators-chelates, and cell surface receptor pairs. Assays involving other specifically bindable substances are also known and within the scope of the present invention.

While many variations have been proposed, one such assay involves binding the analyte in a sample with a specific binding partner previously conjugated with a component of a directly measurable labelling or tagging reaction. The labelling reaction is measured to determine the extent of the binding between the analyte and the conjugated specific binding partner, which, depending upon the particulars of the assay procedure, can reflect the amount of the analyte in the sample. Specific binding assays have shown great utility in determining various ligands in biological, medical, environmental and industrial applications.

A variety of labelling reactions have been proposed for use in specific binding assays, including radioactive, chromogenic and luminogenic procedures. In a radioactive labelling procedure, the component conjugated with the specific binding partner is an atom or molecule which emits radioactivity. Chromogenic and luminogenic labelling reactions are chemically more complex, in that several reactants may be involved. In one type of chromogenic or luminogenic reaction, a molecule changes color or emits light in a catalyzed reaction. The component conjugated to the specific binding partner can therefore be either one of the reactants, termed a substrate, or the catalyst. The remaining components of the reaction, that is, those not conjugated to the binding partner, are supplied in a chromogenic or luminogenic reagent medium, so that the uniting of the labelled conjugate and the reagent medium results in the desired color change or light emission, respectively.

A variety of assays using the principles of the specific binding approach are known, and several have become important diagnostic tools. In one such type of specific binding assay, the immunoassay, the analyte is an antibody, antigen, or hapten, and is made to react with another member of this group. The remaining background discussion will focus on such immunoassays, although this focus is made for clarity of presentation, and is not to be interpreted as limiting of the invention, which is broadly applicable to luminescently labelled specific binding assays.

Detecting the presence of reactive components in the body is a medically important diagnostic technique particularly suited to use of specific binding assays. In one important example, the immune reaction, the human body responds to certain foreign molecules called antigens by itself producing antibodies specific to the antigens, which help counteract the invading antigens. Some persons develop exaggerated responses to even small amounts of certain antigens. These reactions, which may be severe or even fatal, are termed allergic reactions. It is therefore highly desirable to be able to determine whether a person has allergies, and, if so, to what antigens, so that exposure can be avoided or so that the person may be desensitized to the antigen.

In the past, allergic sensitivity was measured by in vivo patch or stratch tests, wherein a possible antigenic irritant is contacted to the person's skin for a period of time, and the sensitivity judged by observing the skin reaction. As well as being imprecise and difficult to quantitate, such in vivo tests are expensive, inconvenient and time consuming for both physician and patient.

In vitro immunoassays can indicate the allergic condition of a person by determining the level of antibodies specific to certain antigens that are present in a fluid sample drawn from the patient's body. In one specific binding immunoassay for detecting the presence in the human body of antibodies to particular antigens, the antigen is attached to a solid surface designated for measurement and then exposed to human blood serum drawn from the patient, which may or may not contain the antibodies specific to the antigen. If antibodies are present in the serum, they react with the antigen and are thus also immobilized at the solid surface. The serum is removed, and the antigen-antibody pair, if present, is labelled by one of several means. For example, the antigen-antibody pair may be labelled with a radioactive atom conjugated to an anti-human antibody, so that the radioactive atom becomes immobilized at the surface (through the antigen-antibody pair) for subsequent measurement, only if the antibody analyte is present in the serum. This procedure, termed a radioimmunoassay, is effective but has certain drawbacks such as the need to use radioactive reagents which must later be disposed of, and limited sensitivity to low levels of analyte.

It has also been proposed to label the antigen-antibody pair attached to the surface with an anti-human antibody conjugated with one component of a luminogenic reaction system, the procedure being termed a luminescent immunoassay or LIA. The remaining components of the luminescent reaction system are provided in a subsequently introduced reagent medium, so that contacting the reagent medium to the immobilized labelled conjugate results in light emission. The light source for the luminescent assay may be chemical or biological in nature, so that the luminescent assays are respectively termed chemiluminescent and bioluminescent. The light emission in the luminescent assay may also arise from fluorescence or phosphorescence. The light emitted in any of these assays may be detected for measurement by any suitable means, such as, for example, a photomultiplier tube or photographic film.

Several problems arise in the use of luminescent specific binding assays. Of particular concern is the emission of light from a surface or volume other than that which is designated for measurement. Such light, termed extraneous light, interferes with the measurement of the light emitted from the designated surface. In the assay procedure just described, an undesirable extraneous lighting is produced adjacent the solid surface at which the tagged antigen-antibody pairs are immobilized, producing a "halo" effect around this designated surface during luminescence. This extraneous light broadens the apparent image of the surface and reduces its sharpness. The apparent relative intensity of the light emitted from the designated surface is altered as a result of this extraneous lighting. That is, a relatively weakly emitting area of a solid surface may appear to be somewhat brighter relative to the background than it actually is due to the extraneous light, with an apparent relative strengthening and broadening of its image. Inaccuracies of measurement can then result.

A related problem results from nonspecific binding. Although the described specific binding assays are generally highly specific, there may be nonspecific binding wherein a luminescent reaction component becomes immobilized at a surface even though no corresponding specific binding partner is present. If such nonspecific binding occurs, then nonspecific luminescence can be emitted, resulting in a false positive indication of reactivity even in an absence of corresponding analyte in the sample.

In another type of luminescent specific binding assay, an analyte or analyte analog is preferentially concentrated at a designated measurement surface, such as the bottom of a transparent tube wall. A first solution containing the analyte is added before or simultaneously with a specific binding partner for the analyte, conjugated with one component of a luminescent reaction, so that specific binding pairs are formed in solution and at the designated measurement surface. The remaining components of the luminescent reaction are then added in a second solution. However, reactive pairs found at other surfaces and throughout the tube volume, produce extraneous light emission, which can interfere with the measurement of light intensity from those pairs located at the designated measurement surface. One way to reduce such extraneous light is to physically remove the sample and the first solution from the tube before adding the second solution, but this approach necessitates a separation step. The assay thus requires a heterogeneous procedure rather than a homogeneous procedure, thereby increasing the cost of performing the assay. It would be highly desirable to avoid the interference from extraneous light in these circumstances so that the assay may be conducted homogeneously, particularly where many such tests are routinely performed and the separation step accounts for a significant cost.

Accordingly, there has been a need for an approach to suppressing undesirable extraneous light in luminescent assays. The present invention fulfills this need, and further provides related advantages.

SUMMARY OF THE INVENTION

The present invention resides in a technique for suppressing undesirable extraneous light in an assay monitored by luminescent emission. In one such assay, a ligand or analyte in a test solution is bound to a specific binding partner conjugated to one of the components of a luminescent reaction system. The remaining components of the luminescent reaction system are introduced in a subsequently added reagent medium. Specifically, the technique is preferably utilized in conjunction with an assay wherein light is emitted from reactants immobilized at a designated measurement surface. The sharpness and clarity of the image from the surface is enhanced, thereby allowing greater precision in both qualitative comparisons and quantative measurements made from the images, or otherwise measured. Additionally, the occurrence of false positive indications is reduced. Extraneous light from non-designated surfaces or volumes is also suppressed.

In accordance with the invention, an attenuator which absorbs light at wavelengths including that of the emitted luminescence is provided in the reagent medium which supplies the last remaining components of the luminescent reaction system not conjugated to the specific binding partner. The attenuator is present in an amount sufficient to suppress the undesirable extraneous light otherwise visible from surfaces or volumes other than the designated measurement surface or volume.

In one embodiment, as the light produced by the luminescent reaction is measured, the designated surface is in contact with the luminescent reagent medium. The reagent medium includes an attenuator which suppresses the extraneous light. Preferably, the attenuator is a dye that absorbs light of at least the wavelength of the light emitted by the luminescent molecules. In suppressing the extraneous light, the attenuator also reduces or eliminates the nonspecific luminescence.

The attenuator added to the reagent medium may conveniently be chosen as a dye which absorbs light over a spectrum of wavelengths, including at least the wavelength of the light emitted in the luminescent reaction. The attenuator optionally absorbs light at other wavelengths, and there is no limitation that the quencher absorb light only at the wavelength of the emitted light. As an example, which is not to be taken as limiting the invention in any respect, the luminescent molecule luminol when oxidized emits radiation over a narrow spectrum centered at about 450 nanometers (nm) wavelength. The attenuator should absorb light at this wavelength and additionally should absorb light of a sufficiently broad range of wavelengths about 450 nm to absorb the light from the entire spectrum of the luminol emission. For this case, the preferred attenuator is a dye mixture which absorbs light between 350 nm and 575 nm, to ensure the absorption of the spectrum of luminol emission which is maximal at about 450 nm. The use of such an attenuator suppresses the undesired extraneous lighting otherwise observed adjacent the designated measurement surfaces.

It will now be appreciated that the use of attenuators represents a significant advance in the field of luminescent specific binding assays. The attenuator is included in the reagent medium, suppressing undesirable extraneous light and resulting in sharper images and more accurate measurement of intensitites from designated measurement surfaces. Where the designated measurement surface, from which the luminescence is emitted, is immersed in a liquid reagent medium as the emitted light intensity is being recorded, the attenuator may conveniently be chosen as a dye or a mixture of dyes for inclusion in the reagent medium. Other features and advantages of the present invention will become apparent from the following more detailed description, taken in conjunction with the accompanying drawings, which illustrate, by way of example, the principles of the invention.

BRIEF DESCRIPTION OF THE DRAWINGS

FIG. 1 is a perspective view of a test chamber used in a luminescent assay in conjunction with a first embodiment of the invention;

FIG. 2 is a fragmented, enlarged sectional view of the test chamber of FIG. 1, taken generally on line 2—2;

FIG. 3 is a further enlarged detail view of a portion of FIG. 2;

FIG. 4 is a photographic image of the results of a luminescent immunoassay of a test serum using the test chamber of FIG. 1, without the addition of an attenuator;

FIG. 5 is a photographic image of the results of a luminescent immunoassay of the same test serum as used to obtain the test results depicted in FIG. 4, using the test chamber of FIG. 1, and with the addition of an attenuator in accordance with the invention;

FIG. 6 is a photographic image of the results of a radioimmunoassay of the same test serum as used to obtain the test results depicted in FIG. 4, using the test chamber of FIG. 1;

FIG. 7 is a sectional elevational view of a beaker having generally spherical solid surfaces immersed therein, used in conjunction with a second embodiment of the invention; and FIG. 8 is a sectional elevational view of a tube having a reactive component coated on an inside wall surface thereof, used in conjunction with a third embodiment of the invention.

DETAILED DESCRIPTION OF THE PREFERRED EMBODIMENT

In a first, preferred embodiment of the present invention, an attenuator is used in conjunction with a luminescent immunoassay procedure wherein a plurality of solid threads having a single type of antigen bound to each thread are mounted in a test chamber 10, and exposed to a serum possibly containing antibodies to some of the various antigens. Where an antibody specifically bindable to the antigen on a particular thread is present in the serum, it binds to the antigen and may subsequently be tagged for observation. The luminescent molecule may be of any appropriate type, but a chemiluminescent molecule such as luminol is preferred.

More specifically, FIGS. 1 and 2 illustrate a test chamber configuration suitable for use in the preferred luminescent assay procedure. The test chamber 10 is an elongated rigid hollow pipette made of any suitable nonreactive material, such as polystyrene. A body 12 of the test chamber 10 has a flat face 14 suitable for flush contact to another flat surface (not shown). A portion of the volume of the test chamber 10 adjacent the flat face 14 is hollow, thereby forming an elongated, flat-bottomed cavity 16. A first hollow tubular projection 18 and a second hollow tubular projection 20 are provided at the opposed ends of the test chamber 10. Each of the tubular projections 18 and 20 communicates with the cavity 16 at a point adjacent the respective projection, so that fluid may be drawn into the cavity 16 through the second projection 20, by applying a partial vacuum to the first projection 18. A typical test chamber 10 has a length of about 17 cm, a width of about 1.4 cm, and a height of about 0.8 cm. The cavity 16 is a straight sided, flat-bottomed depression about 11 cm long, about 0.9 cm wide, and about 0.1 cm deep, opening to the 17 cm by 1.4 cm flat face 14 of the body 12. The cavity 16 has a volume of about 1 ml.

A plurality, preferably about 38, of spaced-apart, antigen-coated cotton threads 22 are stretched crossways over the cavity 16 with their ends fixed to the body 12 on either side of the cavity 16. Each thread 22 is prepared by coating a length of cotton thread with a known amount of an antigen whose reactivity with the serum is to be determined. Exemplary antigens include ragweed pollen, certain grasses such as Bermuda grass, certain trees such as ash, and animal components such as cat fur, which may be attached to the thread by any of a number of suitable techniques known to those skilled in the art. Some of the threads 22 may be coated with specific reactants of known reactivity or may be left uncoated, in either case acting as a control or standard to assist in calibration of the test results. Although the threads 22 are described in this embodiment as being coated with antigens, it will be recognized that the test chamber 10 and the test procedure to be described infra may be used generally in conjunction with specific binding assays. In particular, the attenuators of the present invention are not limited to use with immunoassays for antibodies, but may be broadly used for other specific binding assays as described previously.

The cavity 16 is closed with a light-transparent window 24 placed over the open face of the cavity 16 and over the threads 22 so that the threads 22 are inside the closed cavity 16. The window 24 is attached to the flat face 14 of the body 12 by any suitable technique such as an adhesive, solvent bonding, or ultrasonic bonding. In the procedure to be described subsequently for obtaining luminescent intensity measurements, it is desired that intensity be measured only as to light emitted from a designated measurement surface 28 portion of the thread 22, the designated measurement surface 28 in this case being that portion of the surface of the thread 22 contacting or closely adjacent an inner surface 26 of the window 24. Measurement of light emitted from other portions of the surface of the thread 22 or from other portions of the cavity 16 is undesirable, and such light emitted from surfaces or volumes other than the designated surface 28 is extraneous light. In the illustrated preferred embodiment, the threads 22 are slightly flattened along a portion of the designated surface 28 by contact with the inner surface 26 of the window 24, but such flattening is incidental and is not critical for operability of the invention.

The test chamber 10 may be used in an immunoassay to determine the presence of antibodies to the various antigens, as in the blood of a human patient. A sample of blood is drawn from the patient and a sample of blood serum of about 1 ml volume is prepared by centrifuging the blood. The serum is drawn into the cavity 16 through the second tubular projection 20 by a partial vacuum applied to the first tubular projection 18. The projections 18 and 20 are capped, and the serum is allowed to incubate in contact with the threads 22 for a period of time sufficient to allow reaction of any antibodies in the serum with the antigens bound to the threads 22, the time typically being from about 7 to about 24 hours. During this incubation period, any antibodies present in the serum and reactive with the antigens attached to particular threads 22 bind to the antigens, and thence are immobilized at the threads 22. If no antibodies to an antigen bound to a particular thread 22 are present in the serum, no specific binding reaction occurs to the thread coated with that antigen. Thus, if an antibody to a specific antigen is present in the serum, an antigen-antibody pair is immobilized to the thread 22. If no antibody to a specific antigen is present in the serum, no antibody is specifically bound to the antigen attached to the thread 22. Since many different antigens may be attached to the various threads 22, some threads may have bound pairs while others may not, depending upon the various antibodies present in the test serum. The presence of antigen-antibody pairs 29 bound to a thread 22 is illustrated schematically in FIG. 3 by hair-like projections.

Next, the serum is allowed to drain by gravity from the cavity 16, and the interior of the cavity 16 is washed by flushing a buffered wash solution into the cavity 16 through the tubular projection 18. The wash solution is preferably a phosphate buffered 0.1 percent saline solution having a pH of about 7. The wash solution is drained from the cavity 16 through the second tubular projection 20. The washing procedure is preferably then repeated at least twice, each time with a fresh wash solution, to thoroughly clean out traces of the test serum from the cavity 16.

The presence of bound antigen-antibody pairs, schematically illustrated by numeral 29, is determined by luminescently tagging the pairs, so that the presence of the pair 29 is made visible by the emission of light from the site of the pair. The level of light emission from a portion of the thread 22 is then measured to determine the level of reactivity for the antigen-antibody pairs 29 of each thread. Desirably, the light is measured only from the designated measurement surface 28. However, where the present invention is not employed, extraneous light emitted from other surfaces and volumes is undesirably measured. Use of the present invention allows measurement of light emitted only from such a designated measurement surface 28.

Before describing the steps of the assay procedure, the chemistry of the luminescent reaction system for the reactants of the preferred embodiment will be described briefly. The organic molecule luminol (5-amino - 2,3- di hydro - 1,4- phtalazinedione) emits light at a wavelength of about 450 nm during a reaction with an oxidizer such as hydrogen peroxide. This luminol reaction is catalyzed by an enzyme such as horse radish peroxidase (HRP). To obtain a oracticably measurable light intensity, the three reaction components luminol, HRP, and oxidizer must be brought together. (As used herein, a "component" is any one of the reactants in, or catalysts of, a chemical reaction system. While it is recognized that a catalyst does not itself enter the reaction directly, it is intended that a catalyst be within the scope of the term "component.")

The luminol reaction system may be used to measure the presence and quantity of antigen-antibody pairs attached to threads 22 by conjugating any one of the components luminol, HRP, or oxidizer to an anti-human antibody, reacting the conjugating anti-human antibody to the immobilized antigen-antibody pair attached to the threads 22, and separately providing the remaining components in a reagent medium. Where the antigen-antibody pair is present and immobilized, all three components of the luminol reaction will be present at the thread and light will be emitted. Conversely, where no antibody for a particular antigen is present in the serum, no antigen-antibody pair for that particular thread will be present, the conjugated component not included in the reagent medium will be missing, and no light will be emitted. (An exception to the latter statement is due to non-specific binding, which will be discussed more fully infra.) Although the chemistry of the luminol reaction system was described in detail, the invention is not limited in its application to this reaction system. Generally, luminescent reaction systems emit radiation of from about 100 nm to about 1500 nm as a result of internal or external excitation. Other luminescent systems with which the present invention may be used include, by way of example, the following luminescent materials: diacylhydrazides other than luminol, acridinium salts, and diaryl oxalates; and bioluminescent systems such as luciferin and flavin mononucleotide. Other exemplary systems are listed in the disclosure of U.S. Pat. No. 4,396,579, which is incorporated by reference. The present invention is applicable to all such luminescent tagging reactions, whatever the source of the light, and no system limitations are presently known.

In the preferred embodiment, the catalyst in the luminol reaction is provided to the reaction system by conjugating HRP to anti-human IgE, the HRP thus becoming the tag or label. This labelled conjugate is prepared by a standard technique, such as that described by Nakane and Pierce, *Journal of Histochemistry and Cytochemistry*, Vol. 14, page 929 (1967).

Again referring to the presently preferred embodiment, after the serum is removed and the cavity 16 washed, the solution of HRP conjugated to anti-human IgE is drawn into the cavity 16 through the second tubular projection 20. The solution is retained in the cavity 16 for a time sufficient to allow anti-human IgE in the solution to specifically bind with the human antibody of the antigen-antibody pair 29 immobilized at the thread 22, typically a period of up to about 24 hours. HRP is thereby immobilized by the antigen-antibody pairs, where present. However, a minor amount of conjugated HRP may be bound non-specifically to some threads 22, even if no antigen-antibody pairs are present on that thread.

After incubation, the medium containing the remaining unreacted HRP conjugated with anti-human IgE is drained from the cavity 16 through the second tubular projection 20. The cavity 16 is preferably washed at least three times with fresh solutions of phosphate buffered saline, in the manner described previously, to remove traces of unbound HRP.

The cavity 16 is then filled with a reagent medium containing luminol and hydrogen peroxide, preferably 5 millimolar (mM) luminol and 1 mM hydrogen peroxide in 100 mM borate buffer at a pH of about 9, to supply the remaining components of the luminol reaction system. At reaction sites on the threads 22 where HRP was immobilized in the prior steps, all three components of the luminol reaction system are present, the luminol reaction occurs, and light is emitted from that site. Where no HRP is bound, the luminol reaction is not catalyzed, and substantially no light is emitted even though luminol and hydrogen peroxide are present in solution.

The light-emitting molecule itself need not be bound to the thread 22, but instead may be free in the reagent medium. It is understood that the terms "emitted from a surface" and "localized" reaction as used herein can refer to a light-emitting component immobilized at a surface, but can also refer to an unbound light-emitting component free in solution that is sufficiently close in proximity to a surface to permit a component bound to the surface to enter into or catalyze a reaction involving the light-emitting component. The term "tagging" as used herein refers to a procedure wherein one of the components necessary for the light-emitting reaction is directly or indirectly joined to the analyte to be measured such as the antigen-antibody pair attached to a surface. "Tagging" is therefore not limited to the physical attachment of the light-emitting molecule to a ligand.

To produce and record the luminescently emitted light, the tubular projections 18 and 20 of the test chamber 10 are sealed, with the reagent medium in place in the cavity 16. The test chamber 10 is contacted to a piece of film 30 with the flat face 14 pressed against the film 30, in the dark. The film is preferably Polaroid type 57 instant film, available from Polaroid Corporation, Cambridge, Mass. The film is exposed for a period of time sufficient to record the light emitted from the luminol reaction, usually from about 1 second to about 2 hours, and preferably from about 5 minutes to about 40 minutes. The film is processed, and the image analyzed to determine the extent of antigen-antibody pairs bound to each thread 22. Alternatively, the light may be measured by any other suitable means such as the eye, a photomultiplier, or other photodetector.

FIG. 4 illustrates a typical image obtained from the process as described above. White lines are images of threads 22 and indicate the presence of antigen-antibody pairs bound to the threads. The stronger the intensity, the greater the reaction of the patient to the antigen present on that particular thread. As seen in FIG. 4, there is a considerable blurring about the images of many of the threads due to extraneous light, this blurring sometimes being known as a "halo". FIG. 6 illustrates the corresponding image for the same serum, but labelled by radioimmunoassay procedures. The luminescent labelling procedure results in the appearance of some lines not present in film produced by radioimmunoassay. Although the luminescent procedure has higher sensitivity and may therefore produce some lines not seen in the radioimmunoassay procedure, it is also possible that some of the lines observed with the luminescent procedure of FIG. 4 (but not with the radioimmunoassay procedure of FIGURE 6) are false positive indications, resulting from nonspecific binding. Thus, the luminescent procedure described above suffers from the drawbacks of extraneous light, and uncertainty due to the possible presence of false positive images.

In accordance with the present invention, an attenuator which absorbs light of at least the wavelength of the light emitted by the luminescent reaction system is included in the reagent medium, so as to be present during the recording of the emitted light. The attenuator is present in an amount sufficient to suppress the undesirable extraneous light that is otherwise present adjacent many of the threads 22. Preferably, for use with the luminol reaction the attenuator is a mixture of commercially available dyes which absorb light at about the wavelength of light emitted in the luminol reaction, 450 nm. The dye is included in the reagent medium in an amount sufficient to suppress the extraneous light. The attenuator is also found to reduce the observance of false positive indications, thereby improving the reliability of the technique.

Absorption spectra of a number of dyes were measured to determine an acceptable dye or mixture of dyes having an absorption spectrum including the wavelength or wavelengths of light emitted in the luminescent reaction. The dyes were obtained as FD&C (Food, Drug and Cosmetic approved) food dyes having the brand name Schilling from McCormick Corporation, Baltimore, Md. It was observed that Schilling yellow dye has an absorption peak at about 420 nm, and Schilling red dye has an absorption peak at about 520 nm. The Schilling yellow dye contains a mixture of FD&C yellow dye #5, also know as tartrazine, and FD&C red dye #40, also known as Allura ® Red AC. Tartrazine and Allura ® Red AC are respectively entries nos. 8847 and 276 in the Ninth Edition of the Merck Index, which entries are herein incorporated by reference. The Schilling red dye is a mixture of FD&C red dye #3, also known as erythrosine, and FD&C red dye #40, also known as Allura ® Red AC. Erythrosine and Allura ® Red AC are respectively entries nos. 3615 and 276 in the Ninth Edition of the Merck index, which entries are herein incorporated by reference. It is emphasized, however, that use of these specific dyes is not critical to the practice of the invention. Instead, any dye or combination of dyes absorbing light at about the wavelength of the light produced by the luminescent reaction is acceptable, as long as the dye does not adversely influence the assay procedure itself.

Based upon the absorption spectra, the preferred attenuator for the luminol reaction system was chosen as a mixture of equal parts by volume of the tested yellow and red dyes. The absorption spectrum of the mixture indicates light absorption over a spectral range of from about 350 nm to about 575 nm, which range includes the nominal 450 nm wavelength of light emitted by luminol. The attenuator selected should at least absorb light of the wavelength or wavelengths emitted by the luminescent reaction system. Absorption over a spectrum of other wavelengths is permissible, and does not detract from the use of the invention.

The concentration of the attenuator dye in the reagent medium should be sufficient to suppress the extraneous light. While applicant does not wish to be bound by this possible explanation, and operability of the invention is not limited by this possible explanation, the cause of the extraneous light in the embodiment of FIG. 1, as presently understood, is illustrated in FIG. 3. The primary intensity of light reaching the film 30 is that travelling the shortest distance from the designated measurement surface 28 to the film 30, through the reagent medium 32 and the window 24, as illustrated by arrows 34. In the absence of an attenuator some light reaches the film 30 by travelling through greater distances of the reagent medium 32 and the window 24, as illustrated by arrows 36. The light travelling the longer distances (arrows 36) is believed to be emitted primarily from surfaces or volumes other than the designated measurement surface 28 and to cause the extraneous light or halo about the threads 22. The attenuator dye absorbs light by an amount proportional to the distance of travel of the light ray through the reagent medium 32.

The concentration of the attenuator may therefore be selected to absorb an amount of light sufficient to suppress the extraneous light (arrows 36) while having only a minor effect on the light (arrows 34) emitted from the designated measurement surface 28. The selection of the concentration of attenuator therefore involves a balancing between absorbing sufficient light to suppress the extraneous light, and absorbing too much direct light so as to unduly lengthen the photographic exposure time. The functioning of the attenuator is therefore believed to be related to the absorption of emitted light, and not to the selective prevention or quenching of the light-emitting reaction. The attenuator is not a component of the luminescent reaction system, so that selection and optimization of the attenuator for each luminescent reaction system is based upon the physical principles described herein.

A series of measurements was conducted to determine the preferred amount of attenuator dye to be added for the luminol reaction system. Five luminescent assays performed as described above, but with varying dye concentrations, were conducted on portions of blood serum drawn from a single sample. The results were recorded on film, and the intensity of the light emitted from the designated measurement surface 28 of the same control thread measured for each of the five tests, by measuring the voltage signal of a photometer fixed on the designated measurement surface 28. For comparison, the photometer signal immediately adjacent the image of the thread was measured as the extraneous light signal. The following Table I presents the results:

TABLE I

| Relative Concentration Ratio of Dye to Buffer (Nondye) Volume in the Reagent Medium | Positive Thread Voltage (Signal) | Adjacent Blank Film Voltage (Extraneous Light) | Signal to Extraneous Light Ratio |
|---|---|---|---|
| 0 | 4.44 | 2.84 | 1.56 |
| 0.5 | 4.42 | 0.145 | 30.5 |
| 1.0 | 4.36 | 0.110 | 39.6 |
| 2.0 | 3.78 | 0.105 | 36 |
| 5.0 | 2.38 | 0.090 | 26.4 |

Where no dye attenuator is used (concentration ratio of 0), the signal-to-extraneous light ratio is only slightly greater than 1, so that the image of the designated measurement surface 28 does not stand out against the background extraneous light. Increasing dye concentrations decrease the signal from the designated measurement surface 28, as seen in the second column. All attenuator additions significantly reduce the extraneous light, as can be seen from the third column of Table I. The signal-to-extraneous light ratio (fourth column) is maximized when the relative concentration ratio of dye in the reagent medium is about 1.0. The quality and sharpness of the photographic image are improved for all attenuator dye additions studied, but the greatest relative improvement is found for the relative concentration ratio of 1. At this dye concentration, the absorbance for light of 450 nm wavelength is about 8.4. This same optimization technique as described above can be applied to determine optimal concentrations for attenuators used in conjunction with other luminescent reaction systems.

Based upon these results, it was judged that the preferred relative concentration ratio of the 1:1 mixture of red and yellow dye attenuator is from about 0.5 to about 2.0, with the most preferred ratio being 1, corresponding to an absorbance of 8.4. Thus, as used herein, the term "suppression" as applied to extraneous emitted light, does not require complete elimination of the extraneous light, but instead refers to a reduction of the extraneous light intensity relative to the intensity of the light which is intended for measurement. Other dyes, concentrations and ratios may be preferable for other luminescent reactions systems, but these may be readily determined by the procedures set forth above.

A photographic image of the same assay as shown in FIGS. 4 and 6, except that the most preferred relative concentration of attenuator dye is included in the reagent medium, is shown in FIG. 5. The extraneous light is substantially suppressed by the presence of the attenuator, so that the lines on the image are sharp rather than fuzzy and blurred. Only that light emitted from the designated measurement surface of a thread is recorded on the film. Consequently, the intensities of the individual thread images are more truly representative of the quantity of antibody present in the serum than are the corresponding lines of FIG. 4, wherein the fuzziness leads to uncertainty as to image breadth and intensity. It is unexpectedly observed that some lines present in FIG. 4 are not present in FIG. 5. It is believed that the lines present in FIG. 4 but not in FIG. 5 represent false positive indications, probably due to nonspecific binding to the threads 22. That is, nonspecific binding causes a positive indication where none is actually present. This hypothesis is supported by the presence of an image for lines 38 and 40 in FIG. 4 but no corresponding lines in FIG. 5. Lines 38 and 40 are intentionally negative test calibration lines, which should show no reaction and no image intensity. The image of FIG. 5 does not show lines corresponding to lines 38 and 40, and it is therefore believed that the results of FIG. 5, which illustrates use of the attenuator of the invention, are more truly representative of the correct assay results.

The preferred dye may be readily selected as by mixing commercially available dyes of FD&C grade, which do not adversely influence the assay procedure, to obtain an attenuator appropriate for use in conjunction with luminol or light emitters other than luminol. To prepare such an attenuator for use with other luminescent reaction systems, it is necessary only to measure the wavelength of the emitted light for the reaction system, and then select a dye having absorption at that wavelength, or prepare a mixture of dyes which together absorb at the wavelength of the emitted light in the manner previously described. The optimal concentration for the selected attenuator is determined, as by the procedure associated with Table I.

The attenuator of the present invention is economical to use. Only a small amount of a relatively inexpensive attenuator is provided in the reagent medium. No attenuator need be added to the serum, wash solutions, or the medium containing the HRP-conjugated anti-human IgE. If the participants in the luminescent reaction system are provided in a series of media, then the attenuator is added to the medium in place as the light is recorded.

Use of the attenuator of the invention is more economical and effective than the use of masks which might be placed over the window 24 in an attempt to screen out the undesirable extraneous light. Also, masks cannot be used in many assay procedures wherein the solid to which antigen-antibody pairs are immobilized is free to move about. For example, FIG. 7 illustrates a second embodiment wherein glass or plastic beads 40 are placed in a beaker 42, and an assay procedure is conducted using the beads 40 as a solid attachment for ligands 44 being measured. Such an assay might follow a procedure like that described herein for the preferred embodiment, or might follow other assay procedures known in the art. The beads 40 may be free to move about, or even may be introduced or formed during the assay procedure. In these cases, masks are ineffective to reduce extraneous light. On the other hand, the attenuator of the present invention may be added to the reagent medium to suppress the extraneous light, as described previously.

The use of the attenuator of the invention also allows certain specific binding assays to be conducted in homogeneous rather than heterogeneous format. Ordinarily, because the light emitted by a component of a luminescent reaction system in a designated measurement volume or at a designated measurement surface is essentially indistinguishable from that emitted in remote volumes of a test arrangement, the designated measurement volume or surface must be physically separated from the light-emitting components in the remote volume, in order to complete the assay of light from the designated volume or surface without interference from the remotely emitted light. This type of assay is termed "heterogeneous." Where the light emitted from the designated volume or surface can be distinguished from the light emitted from a remote volume, physical separation is not required. The latter is termed a "homogeneous" assay, and is typically less expensive than a heterogeneous assay in that a separation step is not necessary.

For example, as illustrated in FIG. 8, a pair 50 including a reacted analyte from a test sample may be immobilized at an inside surface 52 of a transparent tube 54. A solution containing a binding partner for the analyte, conjugated with one component of a luminescent reaction system, is introduced into the tube 54 and incubated to react the analyte and the labelled anti-analyte conjugate. In conventional practice, the solution containing the remaining unreacted specific binding partner is then removed from the tube 54 and the tube 54 internally washed. In such prior practice, the remaining participants of the luminescent reaction cannot be added directly to the tube 54 while the solution containing the labelled conjugate remains in the tube or while remote volume 58 or remote surface 60 are present, as the components of the luminescent reaction system would mix throughout the volume so that the luminescent reaction would proceed both at the designated measurement surface 56 and also in the remote volumes 58 or at remote surface 60. The degree of reaction at the designated surface 56 could not be separately measured due to interference from extraneous light emitted from the remote volume 58 or remote surface 60.

By contrast, where an attenuator such as a dye is added to the tube 54, as part of the reagent medium containing the remaining participants in the luminescent reaction other than the conjugated label, the extraneous light emitted from remote volumes 58 and remote surfaces 60 is absorbed so that it does not interfere with the measurement of light emitted from the designated measurement surface 56. The test sample and the solution containing the labelled conjugate need not be removed prior to introduction of the reagent medium containing the attenuator, as the extraneous light produced in remote volumes 58 (or remote surfaces 60) is absorbed before it can reach a measurement means such as a piece of film 62. A heterogeneous assay procedure requiring two physical separations is thereby converted to a homogeneous procedure by the use of an attenuator in accordance with the invention.

It will be appreciated that the attenuators of the present invention provide a significant improvement in luminescent specific binding assay procedures. The attenuators are economical and selective to preferentially reduce extraneous light which interferes with the measurement of the light emitted from the designated surface or volume. Those skilled in the art will recognize that variations of the approached described herein may be made within the spirit and scope of the invention. In particular, other luminescent reaction systems and assay procedures may be utilized in conjunction with the invention. Accordingly, the invention is not to be limited except as by the appended claims.

What is claimed is:

1. A reagent medium for use in a liquid phase specific-binding chemiluminescent assay wherein extraneous light is produced, comprising:
   at least one component of a chemiluminescent reaction; and
   an attenuator compound which absorbs light over a spectrum or wavelengths, wherein said spectrum includes the wavelength of said extraneous light, said compound being present in a concentration sufficient to suppress said extraneous light.

2. A medium of claim 1, wherein said attenuator compound is a dye.

3. A medium of claim 2, wherein said attenuator compound is a mixture of red and yellow dyes.

4. A reagent medium for use in a liquid phase specific-binding fluorescent assay wherein extraneous light of a first wavelength is produced, comprising:
   at least one fluorescent compound which absorbs an incident wavelength of light, and emits said first wavelength of light; and
   an attenuator compound which absorbs light over a spectrum of wavelengths, wherein said spectrum includes said first wavelength of light, said compound being present in a concentration sufficient to suppress said extraneous light and said compound unable to fluoresce as a result of absorption of said first wavelength.

5. A medium of claim 4, wherein said medium comprises a single fluorescent compound and said extraneous light is the longest wavelength light produced by said assay.

6. A medium of claim 4, wherein said attenuator compound is a dye.

7. A liquid phase specific-binding luminescent assay producing signal light, which is detected by a light detection device, and extraneous light, of the same wavelength as said signal light, wherein said assay comprises the steps of:
   a) binding an analyte to a surface from which signal light is measured;
   b) binding a specific binding partner to said analyte, said partner being conjugated to a component of a luminescent system; and
   c) introducing prior to measuring said signal light an attenuator compound into a detection solution, wherein attenuator compound absorbs light over a spectrum of wavelengths, said spectrum including the wavelength of said extraneous light, and is added to a concentration sufficient to suppress said extraneous light.

8. An assay of claim 7, wherein said component of a luminescent system is a fluorescent component.

9. An assay of claim 7, wherein at least one of the binding of analyte to surface, binding of partner to analyte, or conjugation of binding partner to component is mediated through an antibody binding site.

10. An assay of claim 7, wherein said component of a luminescent system is a chemiluminescent component.

11. An assay of claim 7, wherein said component of a luminescent system is luminol.

12. A test kit for conducting a luminescent specific-binding assay, said kit comprising chambers containing:
   at least one component of a luminescent reaction system which produces light of a detected wavelength; and
   a reagent medium with an attenuator compound which absorbs light over a spectrum of wavelengths, wherein said spectrum includes said detected wavelength, said compound being present in a concentration sufficient to suppress extraneous light.

13. A kit of claim 12, wherein said kit further includes a test chamber in which the binder assay is performed.

14. A kit of claim 12, wherein said component is a reactive ligand.

15. A kit of claim 14, wherein said reactive ligand is an enzyme-linked antibody.

16. A kit of claim 12, wherein said attenuator compound is mixed with said component.

17. A kit of claim 12, wherein said attenuator compound is a dye, and said component is luminol.

18. A method for suppressing extraneous light arising from other than a designated measuring surface or volume, in a liquid phase luminescent specific-binding assay which measures signal light production of said designated measuring surface or volume, said method comprising a step of:
   a) introducing an analyte to said designated measuring surface or volume;
   b) introducing a specific binding partner to said analyte, wherein said binding partner is conjugated to a luminescent component; and
   c) introducing to said assay before measuring said signal an attenuator compound in an amount sufficient to absorb said extraneous light, but having minimal effect on signal light produced at said measuring surface or volume.

19. A method of claim 18, wherein said luminescent component is a fluorescent component.

20. A method of claim 18 applied to a luminescent reaction system, said method comprising the steps, in order:
   a) introducing a sample containing an analyte into a test chamber which has at least one light-transparent face, said chamber having a substance reactive with said analyte attached to a surface adjacent said face, wherein said sample contacts said surface such that analyte contained in said sample binds to said substance to become positionally immobilized to said surface;
   b) removing said sample and washing said chamber;
   c) introducing into said chamber a specific binding partner for said analyte, said partner being conjugated with a component of said luminescent reaction;
   d) removing unbound partner and washing said chamber;
   e) introducing into said chamber:
      a reagent medium containing reactive components of said luminescent reaction system, thereby producing detectable light, and
      said attenuator compound; and
   f) measuring the intensity of light which passes through said face.

21. A reagent medium for use in a liquid phase luminescent specific-binding assay which produces signal light, at a surface or volume designated for measurement, and extraneous light, from other surfaces or volumes, and medium comprising:
   a) at least one reactive component of a luminescent reaction; and
   b) an attenuator compound which absorbs light over a spectrum of wavelengths, wherein said spectrum includes the wavelength of light produced by said luminescent reaction, said compound being present in a concentration sufficient to absorb said extraneous light before reaching a detection device, while permitting detection of signal light produced from a desired position.

22. A reagent medium of claim 21, wherein said signal light and said extraneous light have the same wavelength.

* * * * *

UNITED STATES PATENT AND TRADEMARK OFFICE
CERTIFICATE OF CORRECTION

PATENT NO. : 5,082,768

DATED : January 21, 1992

INVENTOR(S) : Burd, et. al.

It is certified that error appears in the above-identified patent and that said Letters Patent is hereby corrected as shown below:

Column 7, line 43, delete "oracticably" and substitute therefor, --practicably--;
Column 15, line 14, delete "binder" and substitute therefor, --binding--;
Column 15, line 28, delete "of" and substitute therefor, --at--;
Column 16, line 30, delete "and" and substitute therefor, --said--.

Signed and Sealed this

Fifteenth Day of June, 1993

Attest:

MICHAEL K. KIRK

*Attesting Officer*    Acting Commissioner of Patents and Trademarks